United States Patent [19]
van Berkel et al.

[11] Patent Number: 5,721,125
[45] Date of Patent: Feb. 24, 1998

[54] ENZYMATIC PROCESS FOR PRODUCING 4-HYDROXY-CINNAMYL ALCOHOLS

[75] Inventors: Wilhelmus Johannes H. van Berkel, Wijchen; Edserd De Jong; Marco Wilhelmus Fraaije, both of Wageningen, all of Netherlands

[73] Assignee: Quest International B.V., Naarden, Netherlands

[21] Appl. No.: 571,986

[22] PCT Filed: Jun. 1, 1994

[86] PCT No.: PCT/EP94/01792

§ 371 Date: Jun. 20, 1996

§ 102(e) Date: Jun. 20, 1996

[87] PCT Pub. No.: WO95/02062

PCT Pub. Date: Jan. 19, 1995

[30] Foreign Application Priority Data

Jul. 6, 1993 [EP] European Pat. Off. ............ 93201975

[51] Int. Cl.$^6$ ................ C12P 7/22; C12N 9/02; C12N 1/14
[52] U.S. Cl. ............... 435/156; 435/189; 435/254.5
[58] Field of Search ..................... 435/155, 156, 435/157, 189, 254.5

[56] References Cited

U.S. PATENT DOCUMENTS 5,128,253  7/1992  Labuda et al. ............ 435/147

OTHER PUBLICATIONS

Catalog of Centraalbureau voor Schimmelcultures via the Internet Jun. 11, 1997.

Tadasa, et al: "Initial Steps of Eugenol Degradation Pathway of a Microorganism", Agricultural and Biological Chemistry, vol. 47, No. 11, Nov. 1983 pp. 2639–2640.

De Jong, et al: "Purification and characterization of vanillyl–alcohol oxidase from Penicillium simplicissimum", European Journal of Biochemistry, vol. 208, No. 3, Sep. 15, 1992, pp. 651–657.

Database WPI, Section Ch, Week 9340, Derwent Publications Ltd., Class B05, AN 93–316614 & JP,A,5 227 980, Sep. 7, 1993.

Primary Examiner—Michael G. Wityshyn
Assistant Examiner—Susan Hanley
Attorney, Agent, or Firm—Cushman Darby & Cushman IP Group Pillsbury Madison & Sutro LLP

[57] ABSTRACT

The invention is a process for preparing 4-hydroxy-cinnamyl alcohols by enzymatically oxidizing 4-allyl-phenols using vanillyl alcohol oxidase. The oxidase converts eugenol and chavicol to coniferyl alcohol and coumaryl alcohol, respectively. The vanillyl alcohol oxidase may be obtained from *Penicillium simplicissimum*.

10 Claims, No Drawings

ENZYMATIC PROCESS FOR PRODUCING 4-HYDROXY-CINNAMYL ALCOHOLS

This application is a Section 371 filing based on PCT/EP94/01792, filed Jun. 1, 1994 which in turn is based on EP patent application No. 93 201975.5, filed Jul. 6, 1993.

The invention concerns an enzymatic process for producing 4-hydroxy-cinnamyl alcohol and analogous compounds, hereinafter collectively referred to as 4-hydroxy-cinnamyl alcohols. More particularly the invention concerns an enzymatic process for converting 4-allyl-phenols to 4-hydroxy-cinnamyl alcohols.

4-Hydroxy-cinnamyl alcohols are important intermediates. Thus, 3-methoxy-4-hydroxy-cinnamyl alcohol (coniferyl alcohol) is an intermediate in the synthesis of vanillin which is one of the most widely used aroma components in the food industry. Likewise, 4-hydroxy-cinnamyl alcohol itself (coumaryl alcohol) may be converted to 4-hydroxybenzaldehyde which is also of interest in the flavour industry. Processes known for converting coniferyl alcohol to vanillin include direct conversion such as described in EP-A-0 542 348, or conversion to other intermediates followed by further conversion of those intermediates to vanillin. Thus, coniferyl alcohol may be converted chemically to coniferyl aldehyde. Coniferyl aldehyde in turn may be converted to Vanillin using *Arthrobacter globiformis* mutants as described in DE-A-3604874. Furthermore, coniferyl alcohol may be converted to a suitable ester such as its benzoic acid ester, which in turn can be converted to vanillin, again as described in EP-A-0 542 348.

4-Allyl-phenols may be obtained from various biological sources. Thus, eugenol is an abundantly available starting material e.g. obtained from clove leaf and clove bud oil. On the other hand, various microbiological processes are known for directly converting eugenol into vanillin, see e.g. processes mentioned in DE-A-3604874, using certain *Corynebacterium* or *Pseudomonas* species, and the process described in EP-A-0 405 197.

Furthermore Agricultural and Biological Chemistry, 47 (1983) 2639–2640 discloses that a bacterium isolated from soil, tentatively identified as a *Pseudomonas* sp, acted in the form of a crude extract towards eugenol. After cultivation of this bacterium in the presence of eugenol several metabolites were isolated from the broth and identified as ferulic acid, vanillic acid, procatechuic acid. Subsequently coniferyl alcohol was also identified. The publication suggests that coniferyl alcohol was formed in very small amounts.

Moreover there are two patent applications which are not prior published, but which rely on earlier (first) filing dates than the present application viz. EP-A-0 583 687 (Haarmann & Reimer) which describes the preparation of e.g. coniferyl alcohol from eugenol by using enzyme material from *Pseudomonas sp* with deposit numbers DSM 7062 and DSM 7063 or microorganisms with genetic material therefrom. The yield of coniferyl alcohol reported is 43.5% of the theory according to Example 4.

JP-A-5 227 980 (920035338) (Takasago Perfumery) available as Derwent AN 93-316614 which describes the preparation of at least one of vanillin, coniferyl alcohol, coniferyl aldehyde, ferulic acid and vanillyl alcohol from eugenol by decomposition involving fermentation with a mutant from the *Pseudomonas* genus. The example reports that mutant TK-2102 was cultured in a medium with eugenol and yielded a mixture of vanillyl alcohol, vanillin and ferulic acid and it is noteworthy that there is no mention that coniferyl alcohol was formed.

However, these processes suffer from the disadvantages that they use difficult or inaccessible microorganisms, give rise to many undesirable byproducts or give very low yields. Therefore, an efficient enzymatic or microbiological process for converting eugenol to coniferyl alcohol would be an important step towards an economical process for obtaining vanillin.

It has now been found that various 4-hydroxy-cinnamyl alcohols can be prepared by enzymatic oxidation of the corresponding 4-allyl-phenol using vanillyl alcohol oxidase, an intracellular aryl alcohol oxidase having covalently bound FAD as prosthetic group.

The enzymatic oxidation process according to the invention is depicted in the reaction scheme below:

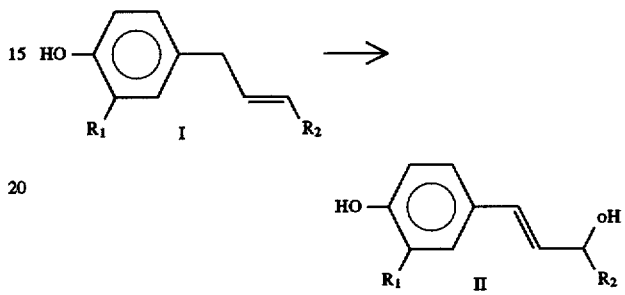

wherein R1 may be H, OH or an alkoxy group with up to 3 carbon atoms and R2 may be H or an alkyl group with up to 3 carbon atoms. Preferably R1 is H or $OCH_3$. Preferably R2 is H. The compounds according to the general formula I for the purpose of this invention are collectively called 4-allyl-phenols, like the compounds of general formula II are collectively called 4-hydroxy-cinnamyl alcohols. The process is particularly useful for converting eugenol into coniferyl alcohol and chavicol in coumaryl alcohol.

Vanillyl alcohol oxidase is induced intracellularly when *Penicillium simplicissimum* is grown on veratryl alcohol. Its isolation and characterization have recently been described in Eur. J. Biochem 208 651–657 (1992). It was described therein to have a substrate specificity limited to vanillyl alcohol and 4-hydroxy-benzyl alcohol, and to oxidize neither other aromatic or non-aromatic alcohols, nor aromatic aldehydes.

The process may be carried out using viable microbial cells containing the enzyme, dead cells, unpurified cell-free extracts or an enzyme preparation obtained by subjecting the cell extract to one or more purification steps such as described in Eur. J. Biochem 208. 651–657 (1992). Preferably cells or a cell-free extract or enzyme preparation obtained from *P. simplicissimum* grown on veratryl alcohol is used.

Also, suitable enzyme preparations may be obtained from other microorganisms after they have been subjected to a genetic engineering process which enables them to make the vanillyl alcohol oxidase. In carrying out such genetic engineering process structural information on the enzyme in *P. simplicissimum* is used.

The process is carried out in solvents usual for such microbial or enzymatic processes, particularly water, at a pH between 7 and 12, preferably between 8 and 11, more preferably between 9 and 11. The temperature of the reaction mixture is kept between 5° C. and 60° C., preferably between 15° C. and 45° C., more preferably between 20° and 40° C.

When live cells are used, the 4-allyl-phenol concentration in the reaction mixture is chosen such as to be non-toxic for the cells, using fed-batch or similar techniques if desired. For dead cells or other enzyme preparations the substrate concentration is preferably chosen below 10 mM, more preferably below 5 mM. The oxygen concentration in the reaction mixture is preferably kept at a level to be non-limiting.

The 4-hydroxy-cinnamyl alcohol may be isolated from the reaction mixture in ways known in the art such as by extraction with an organic solvent. The reaction may be carried out in a suitable two phase system, preferably consisting of an aqueous phase in which the reaction takes place (the reaction phase) and an organic phase chosen such that the reaction product accumulates in the organic phase. Alternatively, the non-reaction phase may be a solid absorbent which absorbs the reaction product from the reaction phase.

EXAMPLE

To 27 μmol eugenol in 7.5 ml 50 mM glycine/NaOH buffer (pH 10.0) was added 1 unit vanillyl alcohol oxidase. The mixture was kept saturated with air and incubated for 3 hours at 35° C. Thereafter the mixture was extracted twice with dichloromethane. The extract was evaporated and the coniferyl alcohol content in the residue analysed gas chromatographically. Eugenol had been converted quantitatively to coniferyl alcohol.

The example was repeated using Chavicol as the substrate. Likewise, it was converted quantitatively to coumaryl alcohol.

1 unit vanillyl alcohol oxidase is the amount of enzyme necessary to oxidize 1 μmol vanillyl alcohol in 1 minute at 30° C. and pH 10.0.

We claim:

1. A process for preparing 4-hydroxy-cinnamyl alcohol according to formula II below which comprises enzymatically oxidizing a 4-allyl-phenol according to formula I in the reaction scheme:

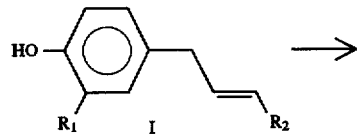

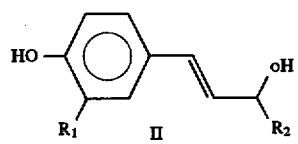

wherein $R_1$ is H, OH or an alkoxy group with up to 3 carbon atoms and $R_2$ is H or an alkyl group with up to 3 carbon atoms, using a vanillyl alcohol oxidase which is an intracellular aryl alcohol oxidase having covalently bound FAD as prosthetic group; and recovering the 4-hydroxy-cinnamyl alcohol.

2. The process according to claim 1 wherein $R_2$ is H.

3. The process according to claim 2 wherein $R_1$ is H or $OCH_3$.

4. The process according to claim 1 wherein the oxidation reaction is carried out at a pH between 7 and 12.

5. The process according to claim 4 wherein the oxidation reaction is carried out between 5° C. and 60° C.

6. The process according to claim 5 wherein the reaction is carried out in a two phase system consisting of a reaction phase and a phase in which the reaction product accumulates.

7. The process according to claim 6 wherein the oxidase is present in viable microbial cells.

8. The process according to claim 1 wherein the oxidase is obtained from *P. simplicissimum* grown on veratryl alcohol.

9. The process according to claim 8 wherein the oxidase is present in dead cells, a cell-free extract or an enzyme-containing composition.

10. The process of claim 1 wherein the oxidase is obtained from *Penicillium simplicissimum*.

* * * * *